(12) United States Patent
Hunkapiller et al.

(10) Patent No.: US 6,258,539 B1
(45) Date of Patent: Jul. 10, 2001

(54) RESTRICTION ENZYME MEDIATED ADAPTER

(75) Inventors: Michael W. Hunkapiller, San Carlos; John H. Richards, Bradbury, both of CA (US)

(73) Assignee: The Perkin-Elmer Corporation, Foster City, CA (US)

( * ) Notice: Subject to any disclaimer, the term of this patent is extended or adjusted under 35 U.S.C. 154(b) by 0 days.

(21) Appl. No.: 09/303,774

(22) Filed: Apr. 30, 1999

Related U.S. Application Data

(63) Continuation-in-part of application No. 09/135,381, filed on Aug. 17, 1998.
(51) Int. Cl.$^7$ ...................................................... C12Q 1/68
(52) U.S. Cl. ..................... 435/6; 435/5; 435/6; 435/7; 435/91.1; 435/91.2; 435/501; 536/26; 536/27; 536/28; 536/77; 536/78; 514/100
(58) Field of Search .............................. 435/6, 5, 7, 91.1, 435/91.2; 436/501; 536/26, 27, 28, 77, 78; 514/100

(56) References Cited

U.S. PATENT DOCUMENTS

| | | |
|---|---|---|
| 4,731,325 | 3/1988 | Palva et al. . |
| 5,242,794 | 9/1993 | Whiteley et al. . |
| 5,631,134 | 5/1997 | Cantor . |
| 5,710,000 | 1/1998 | Sapolsky et al. . |
| 5,800,994 | * 9/1998 | Martinelli et al. ........................ 435/6 |
| 5,858,751 | 1/1999 | Paulson et al. . |

FOREIGN PATENT DOCUMENTS

| | | |
|---|---|---|
| 0735144 A1 | 10/1996 | (EP) . |
| WO 94/01582 | 1/1994 | (WO) . |
| WO 95/04160 | 2/1995 | (WO) . |
| WO 96/41011 | 12/1996 | (WO) . |
| WO 97/27317 | 7/1997 | (WO) . |
| WO 97/31256 | 8/1997 | (WO) . |

OTHER PUBLICATIONS

International Search Report dated Jan. 24, 2000 in PCT / US99 / 18422.

Uhrau, P. and Deugau, K.V., "Non–Cloning Amplification of Specific DNA Fragments from Whole Genomic DNA Digests Using DNA 'Indexers', " Gene 145: 163–169 (1994).

* cited by examiner

*Primary Examiner*—W. Gary Jones
*Assistant Examiner*—Janell E. Taylor
(74) *Attorney, Agent, or Firm*—Scott R. Bortner

(57) ABSTRACT

The present invention relate to methods and compositions for simultaneously analyzing multiple different polynucleotides of a polynucleotide composition comprising multiple diverse polynucleotide sequences. The subject methods and compositions may also be applied to analyze or identify single polynucleotides; however, the subject methods and compositions are particularly useful for analyzing large diverse populations of polynucleotides, e.g., cDNA libraries. Most embodiments of the invention involve hybridizing terminus probes (of known base sequence) to adapter-modified restriction fragment generated from polynucleotide for analysis, and subsequently joining the terminus probes and internal fragment probes to each other. The terminus probe hybridizes to bases of restriction endonuclease recognition site present at the terminus of a restriction fragment generated from the polynucleotide for analysis. The terminus probes and internal fragment probes may be marked so as to facilitate the simultaneous testing of multiple polynucleotides for the presence of many possible nucleotide base sequences. The identity or expression of a particular polynucleotide of interest may be ascertained (or at least partially determined) by producing a short identifier sequence derived from the nucleotide base sequence information obtained from (1) the hybridization of a terminus probe, and (2) the recognition site of a restriction endonuclease used to generate the polynucleotide molecule of interest. Multiple identification sequences may be obtained in parallel, thereby permitting the rapid characterization of a large number of diverse polynucleotides. Parallel processing may be achieved by differentially marking terminus probes or internal fragment probes. Parallel processing may be achieved by using ordered arrays of oligonucleotides that are terminus probes.

27 Claims, 7 Drawing Sheets

US 6,258,539 B1

RESTRICTION ENZYME MEDIATED ADAPTER

RELATED APPLICATION

This application is a continuation-in-part of U.S. patent application Ser. No. 09/135,381 filed Aug. 17, 1998.

FIELD OF THE INVENTION

Embodiments of the invention are in the field of polynucleotide analysis through the use of hybridization and restriction analysis.

BACKGROUND

The cells that constitute different tissues in an organism, although having the same genomic DNA, differ significantly from one another with respect to the specific genes that are expressed and the levels of expression. Differences in gene expression can also be observed when comparing cells that are obtained from a healthy organism and corresponding cells from an organism manifesting a disease state. Other examples of variations in gene expression include changes induced by exposing a cell to a pharmaceutical compound, a toxin, or some other environmental variable. It is of interest to provide methods for analyzing changes in gene expression. Methods of analyzing gene expression find wide use in both research and diagnostics. Additionally, variations exist at the genomic level between cells from different members of the same species, i.e., polymorphisms. Genetic polymorphism may give rise to gene expression difference between species members. Furthermore, polymorphisms may also give rise to phenotypic differences irrespective of the effect of the polymorphisms on transcription. Thus it is also of interest to provide techniques for analyzing nucleotide sequences, including the detection and monitoring of polymorphisms. Moreover, in many instances, it may be of interest to obtain both gene expression data and sequence information in the same experimental procedure. Various embodiments of the invention provide convenient techniques for addressing one or more of these needs for genetic analysis.

SUMMARY

Embodiments of the invention described herein relate to methods of analyzing an individual polynucleotide or a polynucleotide mixture comprising multiple diverse polynucleotides, typically a cDNA mixture formed from an RNA population of interest. Not only is the analysis of RNA populations of major interest in research, such analysis may be used to predict, diagnose, or treat a variety of diseases. Various embodiments of the invention permit the simultaneous analysis of a large number of different mRNA molecules that form a given mRNA population. DNA (including genomic DNA preparations) may also be analyzed by the subject methods. Various embodiments of the invention also permit the convenient isolation of polynucleotides of interest identified through the subject analytical techniques.

In accordance with the description of the invention provided herein, the identity of a particular polynucleotide of interest may be ascertained by producing a short identifier sequence based on the nucleotide sequence information obtained from (i) the recognition site of a restriction endonuclease used to generate a restriction fragment from the polynucleotide of interest, and (ii) the hybridization of a terminus probe of known sequence. In some embodiments of the invention sequence information from other steps such as chain extension sequencing or selective nucleic acid amplification may be used to obtain additional information to produce an identifier sequence. Furthermore, the base sequence information contained within identifier sequences may be used to detect, discover, or compare polymorphic sequences, e.g., SNPs (single nucleotide polymorphisms). Polynucleotide sequence databases may be conveniently searched for previously identified polynucleotide sequences that match or partially match the identifier sequence. Alternatively, the subject methods may be used to "fingerprint" complex polynucleotide populations without the need to generate identifier sequences. The identifier sequences may also be used to develop oligonucleotide primers (or probes) to isolate the polynucleotide from which a specific identifier sequence is derived. Multiple identifier sequences may be obtained in parallel, thereby permitting the rapid characterization of a large number of polynucleotides.

In preferred embodiments of the invention, representative restriction fragments for analysis are joined to adapters prior to contacting terminus probes. The terminus probes used in the subject methods may be identified by a "marker" that is correlated with the known base sequence of the probe oligonucleotide so as to facilitate the rapid characterization of a large number of diverse polynucleotides in parallel. Parallel analysis of multiple diverse polynucleotides may be carried by using ordered arrays of oligonucleotides (terminus probes) such that the position of the oligonucleotides in the array serve as markers to identify the base sequence of the oligonucleotide in the array.

In one embodiment of the invention, methods are provided for analyzing diverse polynucleotide mixtures such as a cDNA mixture generated from an RNA population. Restriction fragments are formed by digesting the polynucleotide population for analysis with a restriction endonuclease. Preferably, the restriction fragments are representative restriction fragments, i.e., restriction fragments generated from the different cDNA molecules in the mixture in such a way that only a single restriction fragment is recovered for each polynucleotide analyzed. By employing representative restriction fragments, quantitative (or semi-quantitative) measurements of the relative amounts of different polynucleotides in a polynucleotide mixture for analysis may be greatly facilitated. One or more adapters may be ligated to the termini of the representative restriction fragments so as to produce a set of adapter-modified representative restriction fragments. The adapter-modified representative restriction fragments may then be optionally amplified in a nucleic acid amplification reaction employing primers specific for the adapters, thereby producing an amplified set of adapter-modified representative restriction fragments. Selective amplification primers may be used as to reduce the complexity of the mixture of adapter-modified restriction fragments brought into contact with the terminus probes. The amplified set of adapter-modified representative restriction fragments (or a corresponding non-amplified set) may then be contacted under nucleic acid hybridization conditions with terminus probes so that hybridization may take place between each of the different adapter-modified representative restriction fragments and each terminus probe present, thereby permitting hybridization of the probe to complementary strands of the matching adapter-modified representative restriction fragments. Terminus probes may be marked by virtue of their location on an oligonucleotide array. An oligonucleotide array comprising a plurality of oligonucleotide features, wherein each feature of the array is a terminus probe, may be used to analyze a plurality of polynucleotides in parallel. After hybridization with the terminus probe, the adapter-modified representative restriction fragments that have hybridized to the array may optionally be extended in a primer extension reaction (e.g., minisequencing), from the template of the hybridized adapter-modified restriction fragment. The array location of adapter-modified restriction fragments that have hybridized to an array of terminus probes may be detected by a variety of methods, such as detectably labeling the fragments before hybridization or through the use of labeled chain terminators in the optional primer extension reaction step. Alternatively, the fragments may be labeled through the use of fluorescently labeled adapters or labeled amplification primers. Thus the probes on the array that have been hybridized to adapter-modified restriction fragments may be determined, thereby serving to identify which of the oligonucleotide features (terminus probes) are complementary to a given representative restriction fragment. Sequence information from the terminus probe hybridized to the adapter-modified restriction fragment may be used to obtain an identifier sequence corresponding to the restriction fragment that hybridized to the array at a given feature. Alternatively, arrays of terminus probes may be used to "fingerprint" complex polynucleotide populations with or without the generation of identifier sequences.

In another embodiment of the invention, terminus probes having array sorting signals are hybridized on an adapter-modified representative restriction fragment (or adapter-modified restriction fragments) and subsequently extended in a primer extension reaction fragments prior to the step of immobilization on a sorting array. The use of sorting arrays permits the step of hybridizing terminus probes to adapter-modified restriction fragments to take place in solution rather than on an array. For example, a representative restriction fragment is formed from a polynucleotide of interest. Adaptors are subsequently joined to the termini of the representative restriction fragment so as to produce adapter-modified representative restriction fragments. Preferably, the adapter-modified representative restriction fragments are amplified in a nucleic acid amplification reaction (e.g., PCR) with primers that specifically hybridize to the two adapters so as to increase sensitivity. A terminus probe is then hybridized to a strand of the adapter-modified representative restriction fragment. The array sorting signals on the internal fragment probes may be used to identify which probe has hybridized to a given adapter-modified restriction fragment by virtue of the ability of the array sorting signal to specifically bind to a receptor for the sorting signal at a predetermined location on an array. A detectable label on an enzymatically incorporated nucleotide may be used to label the terminus probe so that it can be detected after binding to an array sorting signal receptor.

Other embodiments of the invention include kits for carrying out the methods of the invention. The kits comprise two or more reagents necessary for carrying out an embodiment of the subject methods. Embodiments of the kits of the invention may include an oligonucleotide array of terminus probes. The kits may further comprise adapters designed to be used in conjunction with the subject arrays. The inventions also include kits for carrying out embodiments of the invention employing probes that are marked with sorting signals. Kits for use with sorting signals comprise a sorting signal array and internal fragment probes marked with sorting signals for use in conjunction with the arrays. Optionally, the kits of the invention may comprise other reagents required for performing the subject methods, such reagents include, primers, buffers, DNA, polymerases, DNA ligases, and restriction endonucleases.

Figure 1A:
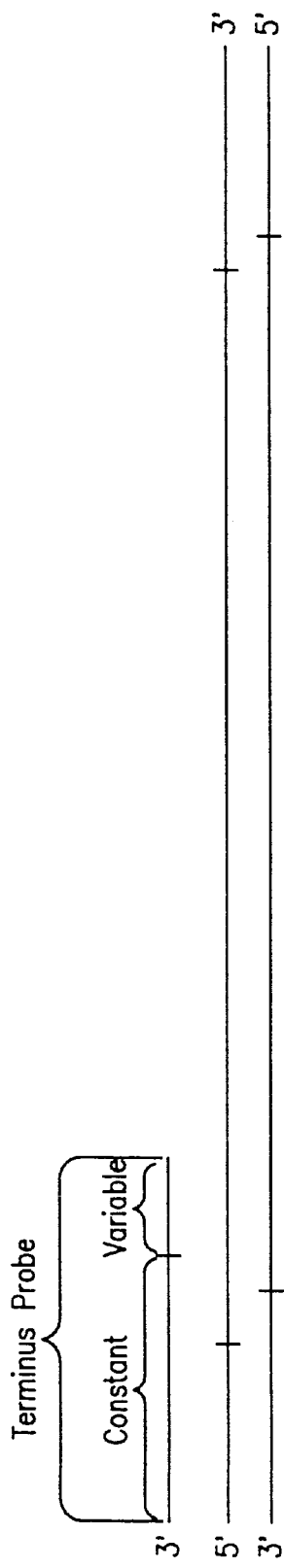
FIGS. 1A and 1B are schematic diagrams showing how terminus probes may hybridize to adapter-modified representative restriction fragments. The variable and constant regions of the terminus probes are indicated. Embodiments of both possible relative orientations of the variable and constant regions on a terminus probe are shown. The vertical lines on the adapter-modified restriction fragments show the actual junctions between the adapters and the restriction fragment. The embodiment in FIG. 1A is suitably for use with primer extension of the terminus probe, whereas the embodiment in FIG. 1B is not.

DEFINITIONS (1.) The term "terminus probe" as used herein refers to an oligonucleotide that is complementary to a specific portion of a strand of an adapter-modified restriction fragment (including restriction fragments that are representative restriction fragments). Terminus probes serve to identify (through hybridization) one or more nucleotides of a restriction fragment that are adjacent to the junction formed between an adapter and a restriction fragment. Terminus probes are complementary to one or more bases adjacent to both sides of the junction. Terminus probes are complementary to bases at and near the junction formed between an adapter and a restriction fragment. Terminus probes may thus be conveniently referred to as complementary to junctions between the adapter and the restriction fragment, even though the actual junction is formed by the juxtaposition of only two bases. Because adapter-modified restriction fragments may have two junctions between adapters and the restriction fragment (one for each terminus of the restriction fragment), the terminus probe may be selected so as to be complementary to nucleotide bases at either of the two junctions (but not both junctions). In many embodiments of the invention, multiple terminus probes are selected to be used in conjunction with one another, i.e., sets of terminus probes, thereby providing for the simultaneous analysis of multiple polynucleotides when the different probes are used in conjunction with one another. The different terminus probes that form a given set of terminus probes are preferably selected so as to hybridize to the equivalent junction and some strands of the different adapter-modified restriction fragments produced in a given embodiment of the subject methods. By "equivalent junction," it is intended that the junction formed between the same adapter and the same restriction fragment terminus be used for all the adapter-modified restriction fragment analyzed by a given set of terminus probes.

Terminus probes are said have a "constant region" and a "variable region." A given nucleotide base in a terminus probe is either in the constant region or the variable region, but not both. The "constant region" is said to be constant because the constant regions of a set of terminus probes are functionally the same as each other with respect to their hybridization specificity as used in the methods of the invention. The constant region is complementary to (1) nucleotides of the restriction endonuclease recognition site used to generate a terminus of the restriction fragment for analysis, and (2) at least a portion (and preferably all) of the adapter adjacent to the restriction endonuclease recognition site at the adapter/restriction fragment junction. The length of the constant region will be, in part, determined by (1) the length of the recognition sequence of the relevant restriction endonuclease, (2) the length of the adapter used in conjunction with restriction fragments, and (3) the number of selective nucleotides present on selective amplification primers (as applied to these embodiments employing selective amplification steps). In embodiments of the invention employing selective primers to amplify a subset of one adapter-modified restriction fragments, the constant region may include nucleotides corresponding to the selective nucleotides of the selective primer. Typically, the length of the constant region is 5–20 nucleotide bases in length. The constant region may extend past the region of the terminus probe designed to hybridize to adapter-modified restriction fragments. Additional probe bases functionally independently of the constant region, but still optionally constant between the different probes, may be used to reduce steric hindrance between solid supports and restriction fragment hybridization. The "variable region" is said to be variable because the variable region of a set of terminus probes have different nucleotide base sequences. The variable region of a terminus probe is complementary to a portion (typically 1–12 nucleotide bases) of the restriction fragment that are adjacent to the restriction endonuclease recognition site base or bases at the terminus of the restriction fragment used to form the adapter-modified restriction fragment.

Figure 1B:
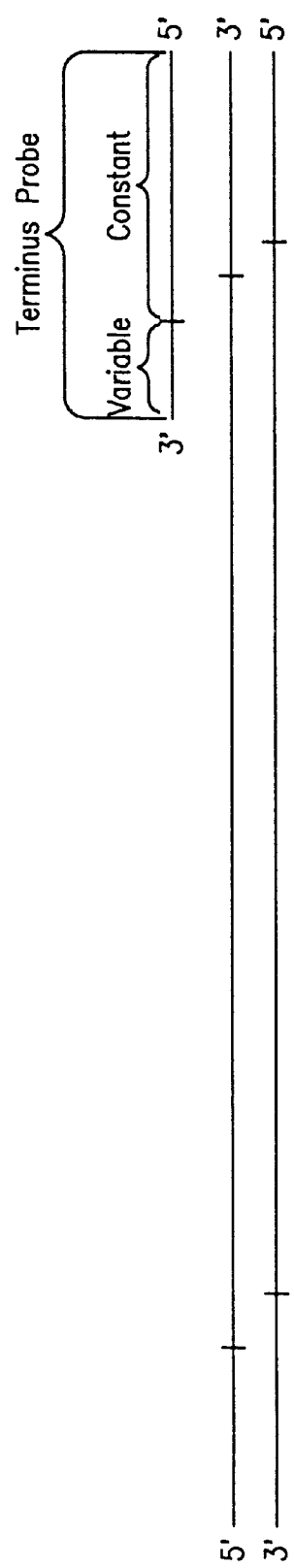
Figure 2:
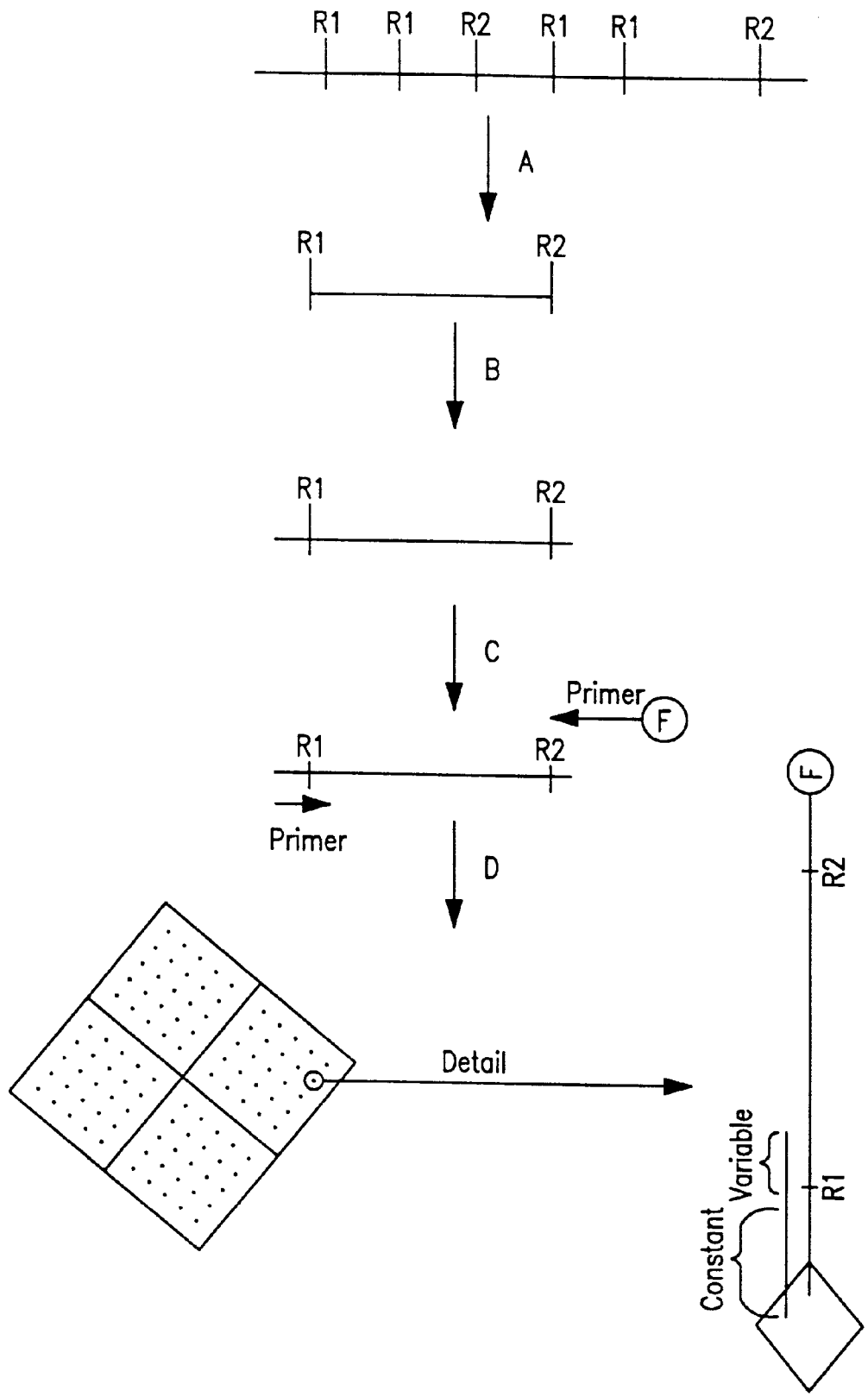
FIG. 2 is a schematic representation of a method of analyzing complex polynucleotides in accordance with the methods of the invention. R1 and R2 are used to indicate restriction sites. Step A indicates the generation of representative restriction fragments from cDNAs. Step B shows the addition of adapters to the representative restriction fragments to form adapter-modified representative restriction fragments. Step C shows the addition of amplification primers and performance of a PCR reaction to generate adapter-modified representative amplification products. One of the amplification primer is marked with fluorescent label (designated by the circled "F"). Step D shows the hybridization of a strand of an adapter-modified representative restriction fragment to a terminus probes of an array. An overview of an array comprising subarrays is shown. The hybridization of the adapter-modified representative restriction fragment is shown as a detailed view of an individual array feature.
Figure 3:
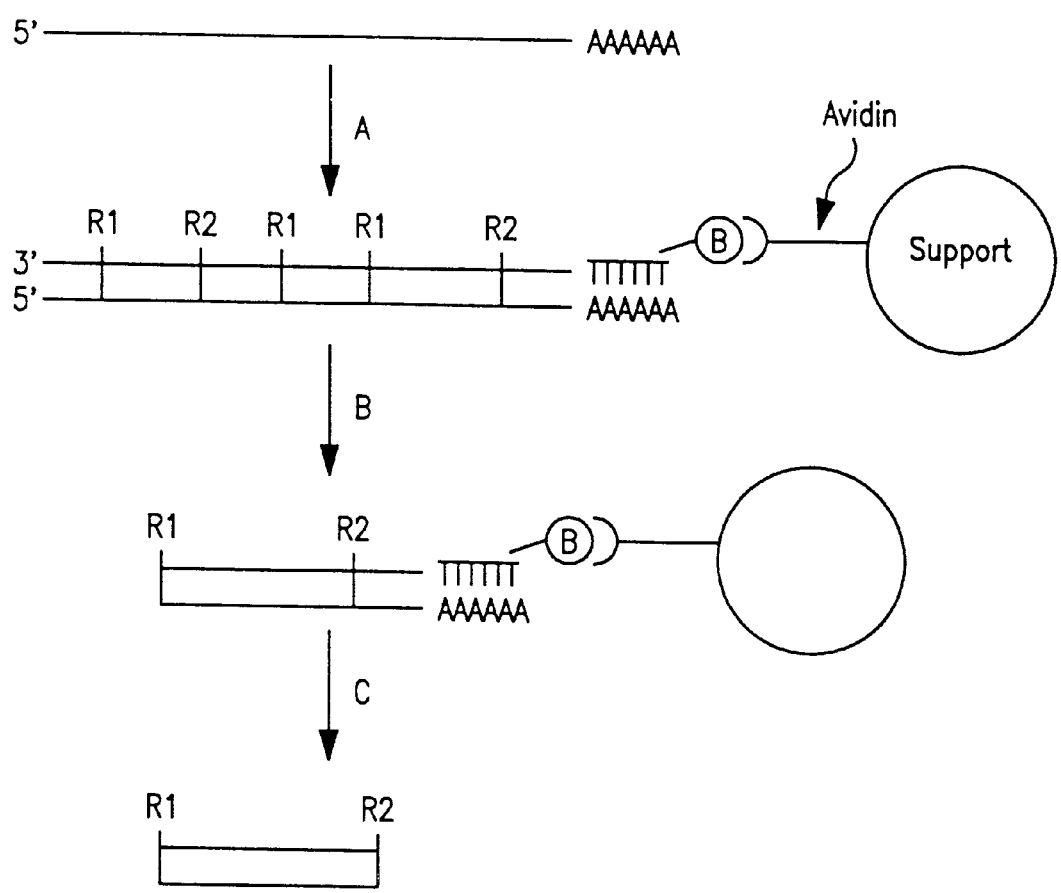
FIG. 3 is a schematic diagram of formation of a representative restriction fragment by sequential restriction endonuclease digestion. In Step A, cDNA from mRNA is formed using a biotinylated poly dT primer and is bound to avidin immobilized on a solid support. The circled B indicates biotin. In Step B, a first restriction endonuclease (R1) is added and the digestion products are removed by washing. In Step C, a second restriction endonuclease R2 is added and the representative restriction fragment is recovered.
Figure 4:
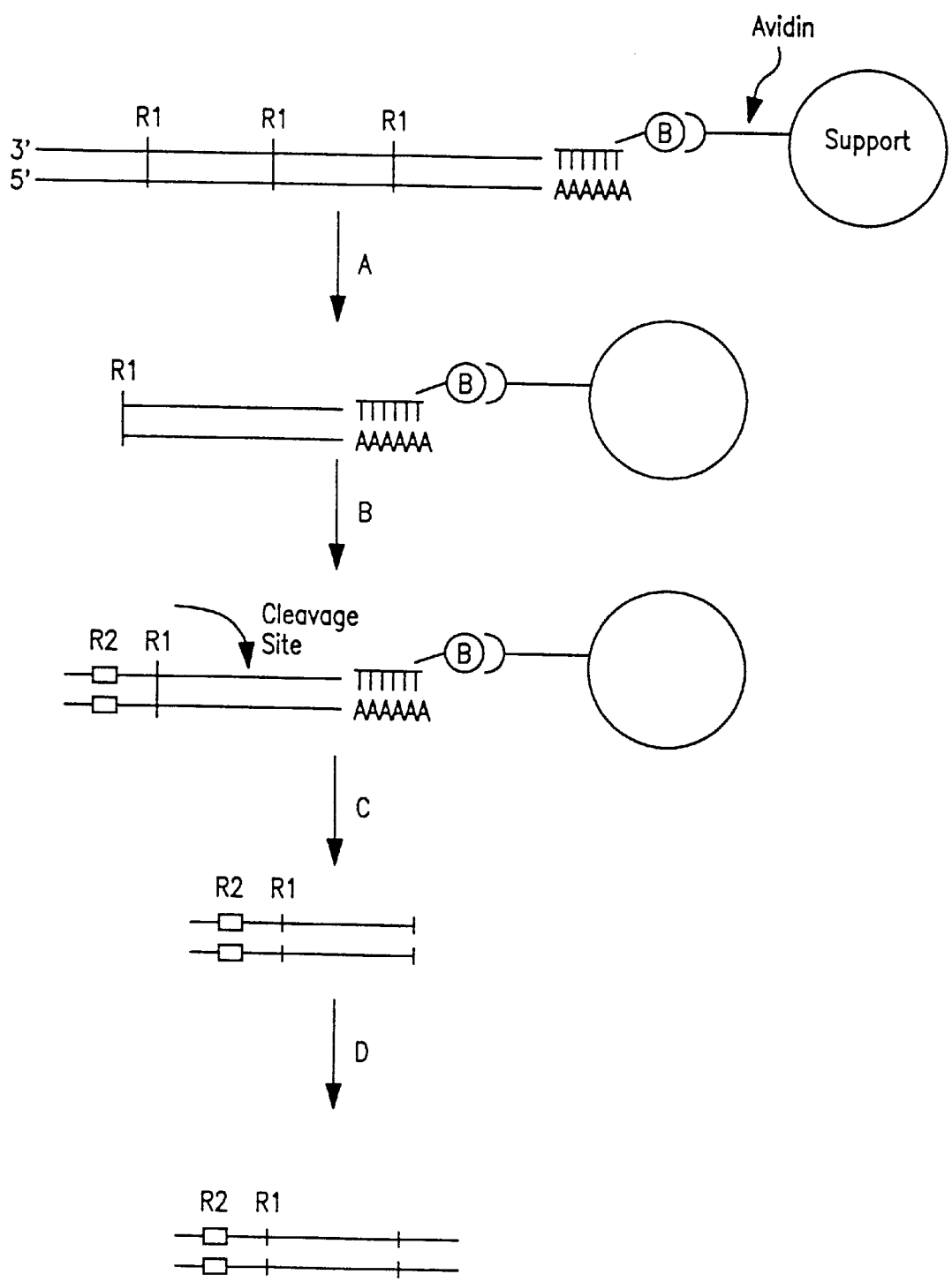
FIG. 4 is a schematic diagram of an embodiment of a technique for generating representative restriction fragments by sequential restriction endonuclease digestion employing a type IIs restriction endonuclease. In Step A, cDNA formed by priming first strand synthesis with a biotinylated poly dT that is bound to avidin immobilized on a solid support is treated with a first restriction endonuclease (R1). In Step B, an adapter having a recognition site (indicated by the bolded rectangle region) for a Type IIs restriction endonuclease (R2). In Step C, the type IIs restriction endonuclease is added and the representative restriction fragment isolated. In Step D, a second adapter is added.
Figure 5:
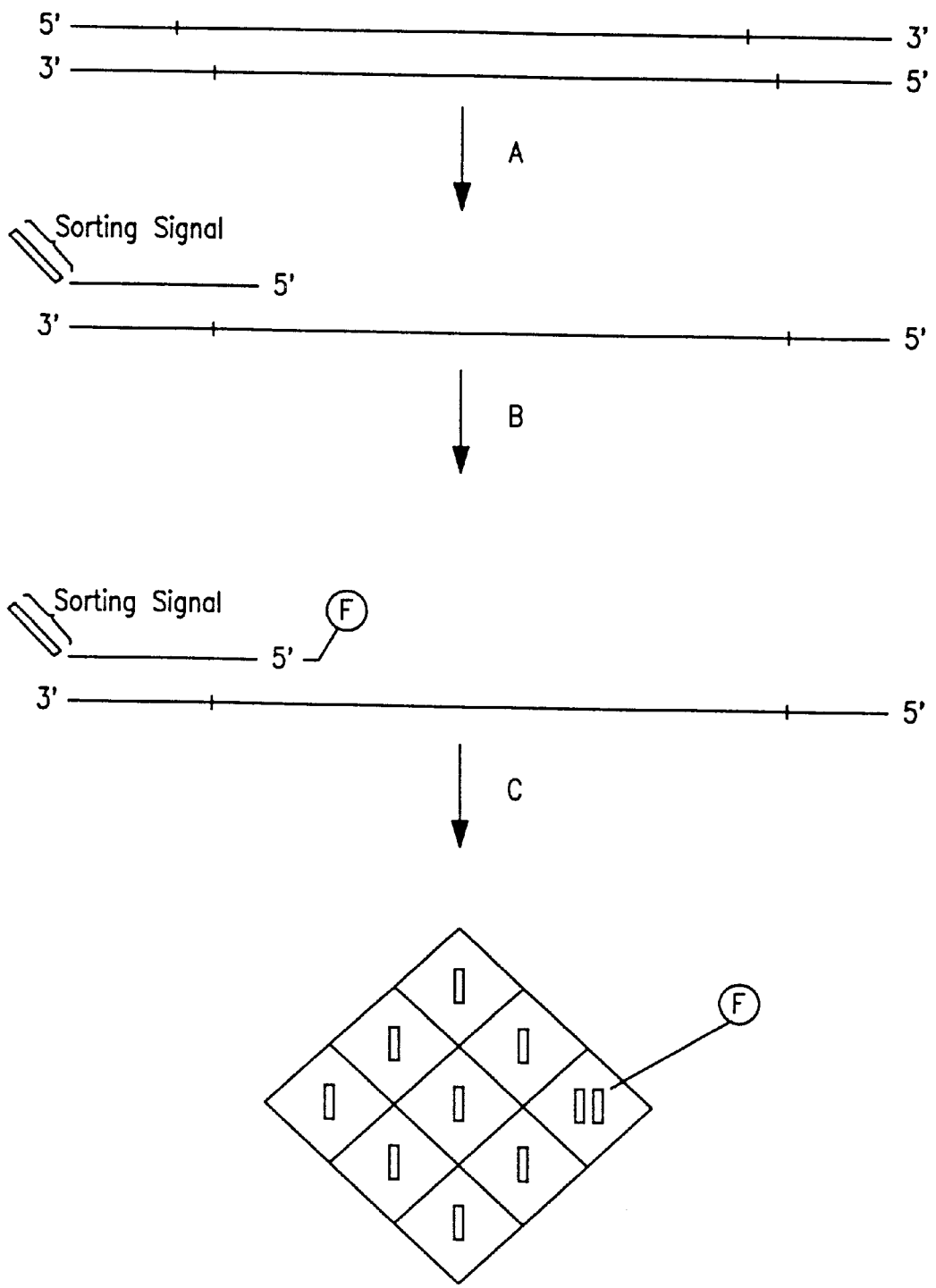
FIG. 5 is a schematic diagram of an embodiment of the invention employing sorting arrays. In Step A, a terminus probe marked with an array sorting signal (indicated by the rectangle on the 3'end of the probe) is hybridized to a strand of the adapter-modified representative restriction fragment. The vertical lines cutting across the adapter-modified restriction fragment indicate the junctions between the adapters and the restriction fragment. In Step B, the terminus probe is extended with a fluorescently labeled 2'3' dideoxynucleotide in minisequencing reaction. In Step C, the extended fluorescently labeled terminus probe is contacted with a sorting array and bound to an array sorting signal receptor at the indicated location on a sorting array. The single rectangles on the array indicate un bound array sorting signal receptors. The double rectangles indicate the bound array sorting signal.
Figure 6:
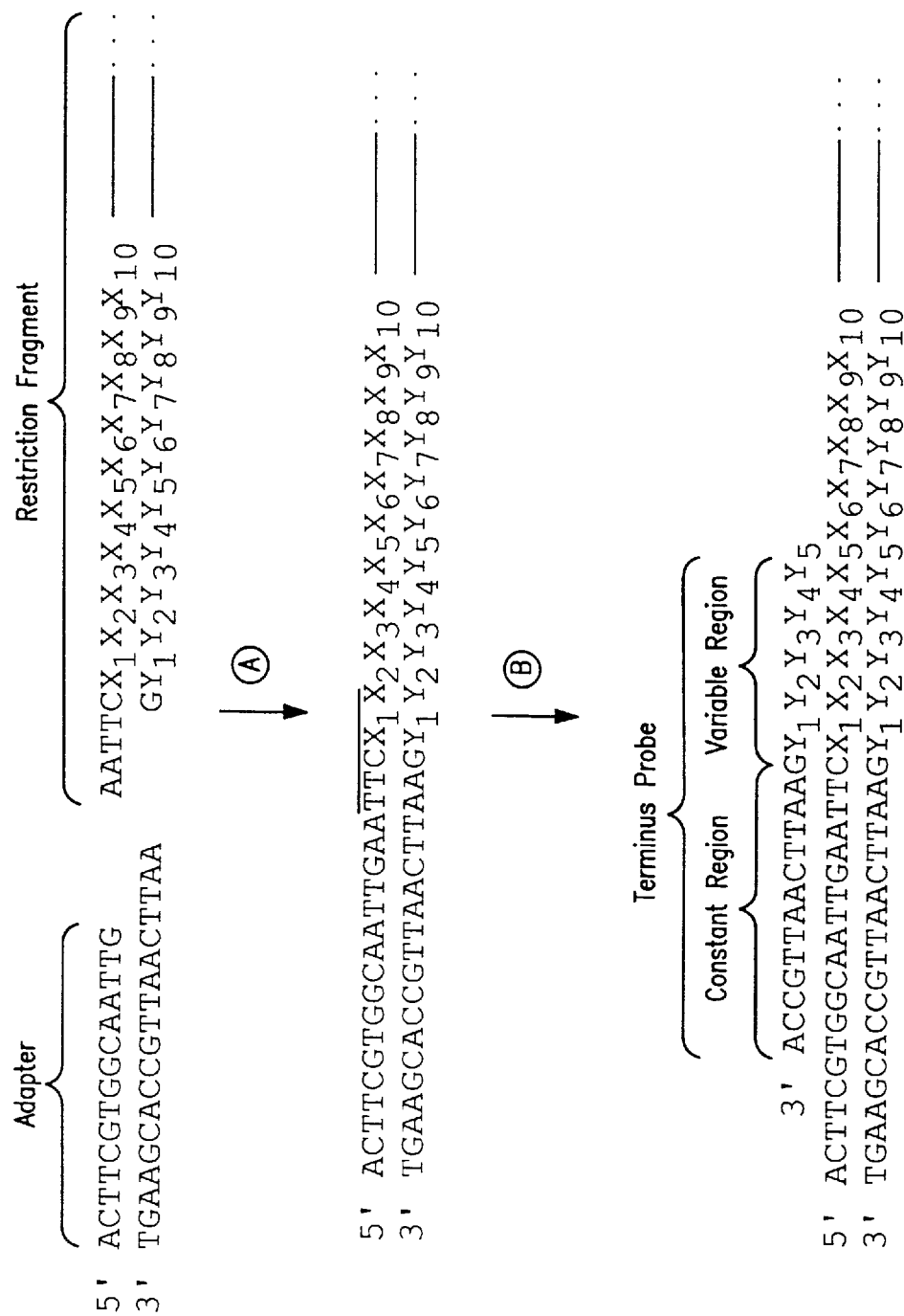
FIG. 6 is a schematic diagram of an example showing the joining of an adaptor (for EcoRI) to a terminus of a representative restriction fragment and showing the orientation of a terminus for use in conjunction with this adapter modified restriction fragment. The Xs represent bases of the restriction fragment, excluding the restriction site bases. The Y's represent complementary bases on the other strand, excluding the restriction site bases. The variable region of the terminus probes is indicates by bases $Y_1$–$Y_5$. The terminus probe is indicated by bases $Y_6$–$Y_{10}$. In Step A, an adapter is joined to a restriction fragment. In Step B, a terminus probe is shown in alignment with the adapter-modified restriction fragment.
Figure 7:
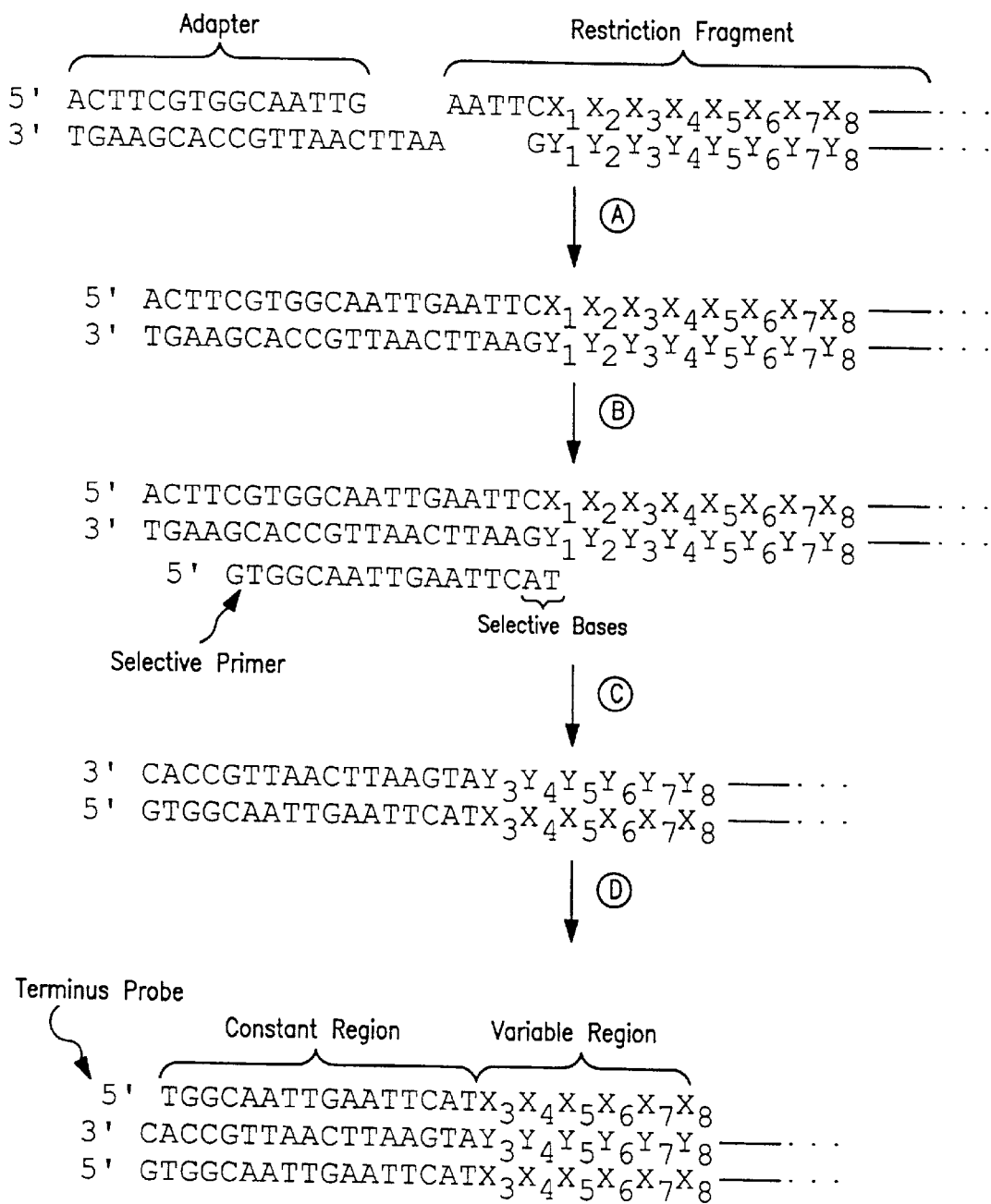
FIG. 7 is a schematic diagram of an example showing the joining of an adaptor (for EcoRI) to a terminus of a restriction fragment and the use of selective primers. The Xs represent bases of the restriction fragment, excluding the restriction site bases. The Ys represent the bases of the complementary strand. In Step A, an adapter is joined to a restriction fragment. In Step B, a selective primer is annealed to the adapter-modified restriction fragment. The "A" and "T" are the two selective bases. In Step C, an amplification formed using the selective primer is shown. In Step D, a terminus probe is annealed to a complementary strand of the amplification product of the selective amplification of the adapter-modified restriction fragment.

The "variable region" of a terminus probe may be located either 5' or 3' with respect to the constant region. The selection of the relative orientation of the variable region with respect to the constant region in a given embodiment of the invention will vary in accordance with choice of which strand of the adapter-modified restriction fragment is selected for analysis and in accordance with the choice of which terminus of the adapter-modified restriction fragment is to be analyzed (see FIG. 1).

(2) The term "a set of terminus probes" as used herein refers to a plurality of different terminus probes used in conjunction with each other, wherein each probe in the set has a functionally identical constant region, e.g., all of the constant regions are identical or have essentially the same sequence-specific hybridization properties, and the variable regions are different from one another. The term "A complete set of terminus probes" refers to a set of terminus probes that includes all possible nucleotide variable sequences (for the four major nucleotide bases, A, C, G, and T, or functional equivalents thereof). All variable regions of the oligonucleotides in a set of terminus probes are the same length. Thus the number of different terminus probes required to form a complete set of terminus probes increases with the length of the variable region. The number of different oligonucleotides required to form a complete set increases with the length of the variable regions in the terminus probes that form a set ($4^N$, wherein N is the length of the variable region).

(3) The term "selective amplification" refers to nucleic acid amplification techniques such as, PCR (the polymerase chain reaction), employing pairs of primers wherein at least one of the primers is a selective primer, and the primers are used in repeated cycles (e.g. temperature change cycles) of nucleic acid synthesis to amplify target molecules. The target used in selective amplification are adapter-modified restriction fragments. The primers used in selective amplification are said to be "selective primers." Selective primers are designed to be complementary (1) to the adapters of adapters-modified restriction fragments, including the junctions between the adapter and restriction fragments (similar to terminus probes complementarily), and (2) complementary to bases of the restriction fragments adjacent to the junction of the adapter and the restriction cleavage site. Typically 1–2, nucleotides of the selective primer are complementary to the bases adjacent to the junction, although it is possible to use more than 3 of these additional nucleotides. These nucleotides that are complementary to bases of the restrictive fragment portion of the adapter-modified restriction fragment are referred to herein as "selective bases." The base nucleotides are located on the 5' end of the selective primers. AFLP analysis as described in European patent application EP 0534858 entitled "Selective Restriction Fragment Amplification: A General Method of DNA Fingerprinting."

(4) The term "oligonucleotide array" as used herein refers to a solid support that has a plurality of different oligonucleotides attached at pre-determined spatial locations on the solid support. The support may be in any of a variety of shapes. In preferred embodiments of the invention, the solid support is substantially planar and the different oligonucleotides are arranged in a two-dimensional matrix. Oligonucleotide arrays may be prepared by a variety of methods well known to those skilled in the art. Such methods include the spotting of oligonucleotides on to the solid support, photolithographically controlled in situ synthesis on the solid support using phosphoramidites with photolabile protecting groups, and in situ synthesis on a solid support using conventional phosphoramidites. Various methods of synthesizing oligonucleotide arrays have described and can be found in, among other places, U.S. Pat. Nos. 5,510,270; 5,405,783; 5,143,854; 5,489,678; 5,733,509; 5,412,087; 5,436,327; and PCT Publication WO 95/25116. There is a predetermined correlation between a given spatial location on the solid support of the array and the particular oligonucleotide located at that given spatial location that is created during the synthesis of the array. Thus, by referring to a particular spatial location on the array, the nucleotide base sequence of the oligonucleotide present at that spatial location may be known.

(5) The term "feature" as used herein with respect to oligonucleotide arrays and sorting arrays refers a group of essentially functionally identical macromolecules, e.g., oligonucleotides, at a pre-determined location on an array.

(6) The term "oligonucleotide" as used herein is used broadly to refer to any naturally occurring nucleic acid, or any synthetic analogs thereof, that have the chemical properties required for use in the subject methods, e.g., the ability to sequence specifically hybridize different polynucleotides. Thus, examples of oligonucleotides include DNA, RNA, phosphorthioates PNAs (peptide nucleic acids), phosphoramidates and the like. Method for synthesizing oligonucleotides are well known to those skilled in the art, examples of such synthesis can be found for example in U.S. Pat. Nos. 4,419,732; 4,458,066; 4,500,707; 4,668,777; 4,973,679; 5,278,302; 5,153,319; 5,786,461; 5,773,571; 5,539,082; 5,476,925; and 5,646,260.

(7) The terms "sorting array" and "sorting subarray" refer to an array formed by an array sorting signal receptors that are attached a fixed pre-determined spatial location on a solid support. There is a pre-determined correlation between a given spatial location on the solid support of the array and the sorting signal receptor located at a given spatial location that is created during the manufacture of the array. Thus, by referring to a particular spatial location on a sorting signal array, the identity of the sorting signal receptor at that particular spatial location may be known. An oligonucleotide array may be an embodiment of a sorting signal array. Preferred sorting arrays for use in the invention are oligonucleotide arrays.

(8) The term "array sorting signal" as used herein refers to a member of a specific binding pair. The second member of the specific binding pair is referred to as an array sorting signal receptor. In a preferred embodiment of the invention, the array sorting signals are oligonucleotides.

(9) The term "array sorting signal receptor" as used herein refers to a member of a specific binding pair. The second member of the specific binding pair is an array sorting signal. In a preferred embodiment of the invention, the array sorting signals are oligonucleotides.

(10) The term "specific binding pair" as used herein refers to a pair of molecules, typically macromolecules, that specifically bind to each other. Each member of the specific binding pair may be referred to as a "specific binding pair member." Examples of specific binding pairs include, complementary oligonucleotides, antibody-antigen pairs, lectin-sugar pairs, receptor-ligand pairs, and the like. Preferably, specific-binding pair members bind to each other with high affinity as well as high specificity.

(11) The term "representative restriction fragment" refers to a polynucleotide restriction endonuclease digestion product that is derived from a larger polynucleotide in such a way as to produce a predetermined constant number, preferably one, restriction fragment for the polynucleotide from which the representative restriction fragment was derived. For example, a representative restriction fragment of a 4.5 Kb cDNA may be a 0.8 Kb subfragment having EcoRI and Hind III generated termini and produced by treating the cDNA with the indicated restriction endonuclease. Although the representative restriction fragments are preferably formed through the use of restriction endonuclease digestions of polynucleotides, it will be appreciated by those skilled in the art that the functional equivalents of representative restriction fragments can be produced by the sequence specific cleavage mechanisms other than the use of restriction endonucleases, e.g., oligonucleotides joined to metallic cations. The term "representative restriction fragment," as used herein may refer collectively to representative restriction fragments, adapter-modified representative restriction fragments, and the amplification products of adapter-modified representative restriction fragments. Those instances in which the term "representative restriction fragment" refers only to representative restriction fragment, will be apparent by virtue of the context in which the term is used, e.g., the subsequent manipulations to be performed on the representative restriction fragment. Similarly, the term "restriction fragment" may be used herein to include "representative restriction fragments" as well as conventional restriction fragments. By virtue of context, it will be apparent to those skilled in the art when the term should be construed to exclude representative restriction fragments.

(12) The terms "restriction endonuclease recognition site" and "recognition site" as used herein refers not only to the nucleotides that form a restriction endonuclease recognition site, but also includes: (1) residual nucleotides that were part of a recognition site and remain after restriction endonuclease digestion, and (2) nucleotides that are complementary to the residual nucleotides that were part of the recognition site and remain after restriction endonuclease digestion (and subsequent manipulations). By virtue of the context in which the term is used, it will be readily understood by a person skilled in the art when term "restriction fragment endonuclease recognition site" refers to complete recognition site and when the term refers to the portion of the recognition site that remains after digestion and subsequent manipulations.

(13) The term "fingerprint" as used herein refers to a set of data relating to a complex polynucleotide population in which the relative concentrations of the different polynucleotide that formed the population are measured.

(14) The term "identifier sequence" as used herein refers to a small (e.g., 10–30 base pairs in length) polynucleotide sequence that is present in a larger polynucleotide. Identifiers sequences may include polymorphic regions such as single nucleotide polymorphisms (SNP's) or repeat sequences. The identifier sequence is of sufficient length to permit the identification of a larger polynucleotide comprising the identifier sequence. The identifier sequence may be of contiguous or non-contiguous base sequence information. Preferably, the identifier is a contiguous sequence of nucleotide bases.

(15) The term "marker" as used herein, refers to a compound or method for tracking the identity of an oligonucleotides of known base sequence. A marker may be specifically associated with a given oligonucleotide, the base sequence of the nucleotide may be determined because of the predetermined correlation between the base sequence of the oligonucleotide and the marker. The specific oligonucleotide associated with a marker is said to be "marked."

(16) The term "adapter" as used herein refers to a double-stranded oligonucleotide having a terminus that is capable of being joined to the terminus of a restriction fragment. The terminus of the adapter may have a 3' overhand, a 5' overhang, or may be blunt-ended. As the terminus of the adapter is designed to be complementary to the terminus of a restriction fragment produced by a given restriction endonuclease, the nature of the terminus of the adapter will vary in accordance with the nature of the termini of the restriction fragments for ligation. The terminus nucleotide moieties of the adapter are selected so as to be compatible with the particular joining method used to join the adapter to the restriction fragment of interest. For example, when the joining is catalyzed by a DNA ligase, the 5' terminal nucleotide is phosphorylated and the 3' terminal nucleotide has a hydroxy group. Adapters for use in the subject methods comprise sufficient additional nucleotide (additional with respect to those nucleotides that are required to form an overhanging terminus) to permit the adapter to be used as a site for primer binding in a nucleic acid amplification reaction, e.g., PCR. In preferred embodiments of the invention, the nucleotide bases of the adapter terminus for joining a restriction fragment are selected so as to not recreate the restriction endonuclease site used to generate the terminus of the restriction fragment. Guidance on the joining of adapters to restriction fragments can be found in, among other places, U.S. Pat. Nos. 5,093,245 and 5,366,877.

(17) The term "joining" as used herein, with respect to oligonucleotides or polynucleotides refers to the covalent attachment of two separate nucleic acids to produce a single larger nucleic acid with a contiguous backbone. Preferred methods of polynucleotide joining are ligase (e.g., T-4 ligase) catalyzed reactions. However, non-enzymatic ligation methods may also be employed. Examples of ligation reactions that are non-enzymatic include the non-enzymatic ligation techniques described in U.S. Pat. Nos. 5,780,613 and 5,476,930, which are herein incorporated by reference.

Descriptions of Specific Embodiments

The present invention relate to methods and compositions for simultaneously analyzing multiple different polynucleotides of a polynucleotide composition comprising multiple diverse polynucleotide sequences. The subject methods and compositions may also be applied to analyze or identify single polynucleotides; however, the subject methods and compositions are particularly useful for analyzing large diverse populations of polynucleotides, e.g., cDNA libraries or genomic DNA preparations. Most embodiments of the invention involve hybridizing terminus probes (of known base sequence) to adapter-modified restriction fragment generated from polynucleotide for analysis. The terminus probe hybridizes (i) to bases of a restriction endonuclease recognition site present at the terminus of a restriction fragment generated from the polynucleotide for analysis, and (ii) hybridizes to bases of the restriction fragment adjacent to the restriction endonuclease recognition site. The terminus probes may be marked so as to facilitate the simultaneous testing of multiple polynucleotides for the presence of many possible nucleotide base sequences, e.g., marker by virtue of polynucleotide array location.

Analysis of polynucleotide populations in accordance with methods of the invention may be used to provide one or more of the following types of information: (1) the nucleotide sequence of one or more polynucleotides in a complex polynucleotide composition, (2) partial nucleotide sequences of one or more polynucleotides in a complex polynucleotide composition, or (3) the relative concentrations of one or more different polynucleotides in a complex polynucleotide composition. Analysis of large complex populations of polynucleotides by the subject methods may be used to produce sufficient information about a polynucleotide population that differences between polynucleotide populations may be ascertained. Thus in some embodiments of the invention, "fingerprints" of a given polynucleotide population may be compared with "fingerprints" of other complex polynucleotide populations so as to determine differences in gene expression between the two populations. In addition to providing fingerprints of complex polynucleotide populations, some nucleotide base sequence information may be obtained for one or more polynucleotides in the population or subregions of a large polynucleotide. An important example of a polynucleotide composition that may be analyzed by the invention is a cDNA preparation derived from an RNA population. The analysis of polynucleotide mixtures, particularly cDNA preparations, has numerous practical uses such as measuring gene expression for diagnostic or research purposes. Of particular interest are embodiments of the present invention that permit the majority of different polynucleotides in an RNA population may be detected. It is also of interest to detect for variations in polynucleotide sequences at numerous genome locations.

The identity or expression of a particular polynucleotide sequence (or gene) of interest may be ascertained (or at least partially determined) by producing a short identifier sequence derived by combining from the nucleotide base sequence information obtained from (1) the hybridization of a terminus probe of known base sequence on a polynucleotide of interest, and (2) the recognition site of a restriction endonuclease used to generate the polynucleotide molecule of interest. Additional information for use in producing an identifier sequence may also be obtained through primer extension of the terminus probe hybridized (e.g., extension with labeled chain terminating 2'3' dideoxynucleotides in a "minisequencing reaction"). Yet more information to be used in the creation of an identifier sequence may be obtained by including the selective bases of identity selective primers used in a selective amplification reaction. The combining of the different base sequence information inputs to produce an identifier sequence may optionally be carried out by a programmable calculating device, e.g., an electronic computer, so as to conveniently automate the process when applied to complex polynucleotide populations. An identifier sequence may consist of contiguous or non-contiguous base sequence information. In a typical embodiment, a terminus probe hybridizes to a strand of an adapter-modified representative restriction fragment at a position that includes the junction between the restriction fragment and the adapter. An identifier sequence may be used to produce oligonucleotide primers or probes to isolate the polynucleotides from which the identifier sequence was derived. Multiple identifier sequences may be obtained in parallel, thereby permitting the rapid characterization of a large number of diverse polynucleotides. Parallel processing may be achieved by differentially marking terminus probes or internal fragment probes. Parallel processing may be achieved by using ordered arrays of oligonucleotides that are terminus probes. In order to probe for all possible sequences in a given region of an adapter-modified restriction fragment (or set of adapter-modified restriction fragments) arrays may contain a complete set of terminus probes, i.e., as possible variable region sequences for a given length are present. However, in many embodiments of the invention, particularly those embodiments in which pre-existing base sequence information exists for the polynucleotides to be analyzed, only partial sets of terminus probes may be used to achieve the desired result.

It may also be of interest to employ terminus probes that comprise an additional oligonucleotide hybridized to the terminus probe (and optionally covalently attached to the terminus probe). This additional oligonucleotide is shorter than the terminus probe and hybridized to a constant region. Adapter-modified restriction fragments may be joined, e.g., ligated, to this additional oligonucleotide. Examples of such double stranded arrays and their use can be found in U.S. Pat. Nos. 5,503,980 and 5,631,134.

Preferred embodiments of the invention employ sets of terminus probes of known sequence that are used in combination to hybridize to restriction fragments for analysis. For example, the restriction endonuclease EcoRI has a 6 base pair recognition sequence. Thus, for example, by combining the sequence information obtained from identifying which the 10 base variable region of a terminus probe that hybridizes adjacent to an EcoRI recognition site, 16 bases of sequence information may be obtained so as to provide a unique identifying sequence that may be used to search sequence databases, prepare hybridization probes, or prepare amplification primers.

In a preferred embodiment of the invention, the restriction fragments for analysis are representative restriction fragments. The use of representative restriction fragments rather than more complex mixtures of restriction fragments minimizes quantitation problems associated with attempting to correlate the analysis of multiple restriction fragments derived from each polynucleotide for analysis. By measuring the quantity of a representative restriction fragment produced from a polynucleotide composition, the quantity of the larger polynucleotide from which the representative restriction fragment was derived may be conveniently measured. Similarly, the relative quantities of different polynucleotides may be compared by comparing the relative quantities of different representative restriction fragments.

The subject methods may optionally include the step of pre-selecting only a portion of the nucleic acid population for analysis, e.g., a cDNA library or genomic DNA preparation. Such pre-selection steps serve to reduce the effective complexity of the nucleic acid mixture exposed to the terminus probes, thereby simplifying analysis and reducing the possibility for errors. Such a pre-selection step may involve a nucleic acid amplification technique such as a PCR. For example a multiplexed region of genomic DNA may be used prior to the step of preparing adapter-modified restriction fragments. Another example of pre-selection would be through the use of a selective amplification reaction employing pairs of selective amplification primers. Another example of pre-selection is restriction endonuclease digestion followed by size separation and recover of only DNA digestion fragments within a pre-determined size range.

Embodiments of the invention include many different methods of analyzing polynucleotides. One embodiment of the subject methods includes the steps of: (1) forming adapter-modified restriction fragment (preferably derived from a representative restriction fragment) from a polynucleotide for analysis, and (2) hybridizing a terminus probe to a single strand of the restriction fragment at a position on the adapter-modified restriction fragment that includes the restriction endonuclease-generated terminus. Terminus probes may be marked so as to facilitate the parallel analysis of multiple constituents of a complex polynucleotide population. Terminus probes are preferably marked by their spatial location on an oligonucleotide array. The markers on the terminus probes may then be ascertained in accordance with the specific marking techniques used.

In a preferred embodiment of the invention, at least one adapter is joined to a restriction endonuclease-generated terminus of a representative restriction fragment to form a adapter-modified restriction fragment. Alternatively, two adapters may be ligated to the two termini of the representative restriction fragments. The adapters are joined to the restriction fragment termini prior to hybridization of the restriction fragments to terminus probes and internal fragment probes. The amplification of the fragment by PCR (or a similar nucleic acid amplification technique) may be achieved through the use of primers that can anneal to strands of the adapters. Additionally, the adapters may be used to recover the restriction fragment from which an identifier sequence is derived, e.g., by performing PCR with a primer derived from the identifier sequence and a second primer specific for an adapter joined to the terminus that did not hybridize to the relevant terminus probe. Furthermore, an adapter may be used as a template for facilitating the hybridization of the terminus probe to the restriction fragments for analysis.

Junctions are formed at the site of joining between the termini of the representative restriction fragment and the adapters. Terminus probes are designed to hybridize to the nucleotides forming one of these junctions, i.e., to hybridize to regions of the restriction fragment and adapter that are adjacent to the junctions. Because the adapters are the same or contain regions with a common or substantially similar polynucleotide sequence, the terminus probes that are used to hybridize to the adapter modified representative restriction fragments have a constant region for hybridizing to the adapter and to terminal restriction endonuclease recognition site. Additionally, the terminus probes have a variable region for hybridizing to the restriction fragment nucleotides adjacent to the restriction endonuclease recognition site at the terminus. In embodiments of the invention employing the step of selectively amplifying adapter-modified restriction fragments, the terminus probes have variable regions that may hybridize to nucleotide bases adjacent to the nucleotide bases that were selectively amplified by the selective bases of the selective primer. The variable regions of the terminus probe may be used to divide the adapter-modified restriction fragments into subgroups based on their base sequences adjacent to a terminal restriction endonuclease recognition site.

In a preferred embodiment of the invention, adapter modified representative restriction fragments are amplified in a nucleic acid amplification reaction, e.g., PCR. The product of the amplification product are referred to herein as "adapter-modified representative restriction fragment amplification fragments." The terms "adapter-modified representative restriction fragment amplification products" and "adapter-modified representative restriction fragments" may be used interchangeably in the methods described herein unless indicated otherwise by the context of usage of the term. A nucleic acid amplification step may be used when the signal from the adapter-modified restriction fragments is not sufficient for the production of useful levels of detectable signal in the given polynucleotide sample for analysis. Also, as previously noted nucleic acid amplification may be used for the process of pre-selecting a portion of a complex nucleic acid population in order to simplify analysis.

Terminus probes as used in the subject methods are identified with a "marker" that is correlated with to the base sequence of the oligonucleotide, i.e, the terminus probe. Thus by identifying the marker specifically associated with a given oligonucleotide, the base sequence of the nucleotide may be determined because of the predetermined correlation between the base sequence of the oligonucleotide and the marker. The marker may take on any of a variety of different forms. Such marker forms include: predetermined locations on arrays, fluorescent tag molecules, chromophore tag molecules, chemiluminescent tag molecules, specific binding pair members, temporally distinct addition of oligonucleotides, and the spatially distinct addition of oligonucleotides. Different forms of markers may be used alone or in combination with one another.

In one embodiment of the invention, the terminus probes marked by virtue of predetermined locations on a solid support, e.g., an oligonucleotide array. Thus by knowing the base sequence of a polynucleotide feature at a particular spatial location of an array, the complementary base sequence of a strand of the adapter modified restriction fragment that hybridizes to the array at the specific location may be ascertained. Thus, the array serves to "spatially" mark terminus probes.

In some embodiments of the invention, spatial marking may be achieved by providing an oligonucleotide array divided into various subarrays, wherein each subarray comprises essentially the same set of oligonucleotides features (in the same or different spatial arrangement from each other). For example, an array of terminus probes having variable regions 5 nucleotides in length may comprise 1024 identical subarrays, wherein, each of the subarrays is identical to each other and is formed by 1024 different terminus probes. The subarrays may be organized in such a way as to permit an oligonucleotide solution to be added to one subarray without contacting the other subarrays. In this example, 1024 internal fragment probes (all possible 5-mer sequences) are separately added to each of the different subarrays. The identity of a specific set of adapter-modified restriction fragments may thus be tracked by virtue of the specific subarray to which it is added. The spatial marking effect of using multiple subarrays may be achieved using an equivalent system multiple distinct arrays on separate solid supports.

Another method of using a "marker" to identify a specific oligonucleotide probe is by means of different detectable labels, e.g., fluorescent dye molecules. Detectable labels are chemical compounds that may be detected in relatively small amounts by virtue of their chemical or physical properties. Detectable labels may take on any of a variety of forms such as fluorescent dyes, chromospheres, chemiluminescent molecules, radioactive isotopes, spin labels, enzymes, and the like. A wide variety of labels and labeling techniques may be used to mark probes, with the identifying criteria that the label/labeling method should not significantly interfere with the hybridization of the probe of other such steps required in the subject methods. The detectable labels may be detected either directly or indirectly. Indirect detection employs a chemical intermediate that produces the signal detected by the actual detection device employed. Examples of indirect labeling include enzymes used with a fluorescent substrate, biotin labels used in conjunction with enzymatically labeled avidin, used in conjunction with fluorescently labeled antibodies, and the like. Chemical tags such as fluorescent dyes and other detectable labels permit multiple oligonucleotides (e.g., internal fragment probes to be used together in the same solution. Detectable labels are also of interest because, depending upon the particular detection scheme employed, they permit the quantitative (or semi-quantitative) detection of the label and hence the quantitative (or semi-quantitative) detection of the probe joined to the detectable label. In a preferred embodiment of the invention, the detectable labels employed are fluorescent dyes. Methods and compounds for attaching detectable labels to oligonucleotides are well known to those skilled in the art. Examples of such methods can be found in Hermanson, *Bioconjugate Techniques,* Academic Press, San Diego (1996); U.S. Pat. Nos. 5,366,860; 5,231,141; 5,188, 937; 4,605,735; 4,667,025; 4,789,737; and 4,820,812. The specific methods and instrumentation suitable for detecting a specific detectable label will vary in accordance with the physical and chemical properties of the label. Such methods and instrumentation are well known by those skilled in the art. Examples of such methods and instrumentation can be found in U.S. Pat. No. 5,324,633 and PCT Patent Application No. WO 95/22068.

In many embodiments of the invention it is necessary to label the representative restriction fragments that ultimately become hybridized to the terminus probes. Such labeling is used to detect which terminus probes have hybridized to which adapter-modified restriction fragments. This labeling may take place either before or after the hybridization step. One method of labeling is to use fluorescent dye labeled adapters to form adapter-modified restriction fragments. Other methods of labeling include the random covalent joining of a fluorescent label to genomic on cDNA prior to or after restriction endonuclease digestion. Another example of labeling is the enzymatic incorporation of biotinylated nucleotides into the polynucleotide for analysis. The biotinylated nucleotide residues can be subsequently detected with labeled avid or streptavidin. Guidance in labeling nucleic acids for hybridization to nucleic acid arrays can be found in, among other places U.S. Pat. Nos. 5,837,832, 5,807,522 and 5,753,439.

An example of one embodiment of the subject methods is as follows. A cDNA library is prepared and treated with sequential restriction digestion to produce representative restriction fragments having EcoRI and Hind III cohesive ends. A first adapter is ligated to the EcoRI ends. A second adapter that is tagged with a fluorescent dye is joined to the Hind III ends. The adapter-modified restriction fragments are subsequently hybridized to an array of terminus probes. The terminus probes of the array all have constant regions that are complementary to the EcoRI adapter. The terminus probes also have 10 base pair variable regions. The array includes a complete set of terminus probes, i.e., all possible variable regions are present $4^{10}$=1,048,576. The locations of fluorescently labeled nucleic acids hybridized to the terminus probes are determined and analyzed. Identifier sequences may be derived from the (i) restriction enzyme recognition site and (ii) the sequence of the variable regions of the hybridized terminus probes.

Another example of an embodiment of the subject methods is as follows. A cDNA library is prepared and treated sequential restriction digestion to produce representative restriction fragments having EcoRI and Hind III cohesive ends. A first adapter is ligated to the EcoRI ends. A second adapter that is tagged with a fluorescent dye is joined to the Hind III ends. The adapter-modified restriction fragments are subsequently hybridized to an array of terminus probes. The terminus probes of the array all have constant regions that are complementary to the EcoRI adapter. The terminus probes also have 10 base pair variable regions. The locations of fluorescently labeled nucleic acids hybridized to the terminus probes are determined and analyzed. Identifier sequences may be derived from the (i) restriction enzyme recognition site and (ii) the sequence of the variable regions of the hybridized terminus probes.

Another example of an embodiment of the subject methods is as follows. A cDNA library is prepared and treated sequential restriction digestion to produce representative restriction fragments having EcoRI and Hind III cohesive ends. A first adapter is ligated to the EcoRI ends. The adapter-modified restriction fragments are subsequently hybridized to an array of terminus probes. The hybridized adapter-modified restriction fragments are subsequently subjected to a chain extension reaction using four differentially fluorescently labeled chain terminators (mini-sequencing). The terminus probes of the array all have constant regions that are complementary to the EcoRI adapter. The terminus probes also have 10 base pair variable regions. The locations of fluorescently labeled terminus probes and the emission spectra of the dye incorporate into each probe is determined and analyzed. Identifier sequences may be derived from the (i) restriction enzyme recognition site, (ii) the sequence of the variable regions of the hybridized terminus probes, and (iii) the identity of the bas incorporated during the chain extrusion reaction.

Another example of an embodiment of the subject methods is as follows. A cDNA library is prepared and treated sequential restriction digestion to produce representative restriction fragments having EcoRI and Hind III cohesive ends. A first adapter is ligated to the EcoRI ends. A second adapter is joined to the Hind III ends. The adapter-modified restriction fragments are subsequently amplified in a PCR reaction using primers capable of annealing to the first and second adapters. The primer capable of hybridizing to the second adapter is tagged with a fluorescent dye. The adapter-modified restriction amplification products are subsequently hybridized to an array of terminus probes. The terminus probes of the array all have constant regions that are complementary to the EcoRI adapter. The terminus probes also have 10 base pair variable regions. The array includes a complete set of terminus probes. The locations of fluorescently labeled nucleic acids hybridized to the terminus probes are determined and analyzed. Identifier sequences may be derived from (i) restriction enzyme recognition sites, and (ii) the sequence of the variable regions of the hybridized terminus probes.

Another example of an embodiment of the subject methods is as follows. A cDNA library is prepared and treated sequential restriction digestion to produce representative restriction fragments having EcoRI and Hind III cohesive ends. A first adapter is ligated to the EcoRI ends. A second adapter that is tagged with a fluorescent dye is joined to the Hind III ends. The adapter-modified restriction fragments are subsequently amplified in a PCR reaction using primers capable of annealing to the first and second adapters, wherein the primer that anneal to the first adapter is a selective primer having 2 selective bases. The adapter-modified restriction amplification products are subsequently hybridized to an array of terminus probes. The terminus probes of the array all have constant regions that are complementary to the EcoRI adapter and the 2 selective bases adjacent to restriction site and present on the selective primer. The terminus probes also have 10 base pair variable regions. The array includes a complete set of terminus probes. The procedure may be repeated for all 16 possible 2 selective base pair combinations. The locations of fluorescently labeled nucleic acids hybridized to the terminus probes are determined and analyzed. Identifier sequences may be derived from the (i) restriction enzyme recognition site, (ii) the sequence of the variable regions of the hybridized terminus probes, and (iii) the selective bases of the selective primer.

In another embodiment of the invention, specific binding pair members may be used to mark the terminus probes. Of particular interest are the use of specific binding pair members, the pair of members being (i) array-sorting signals and (ii) array-sorting signal receptors. In preferred embodiments of the invention, the array sorting signals are single-stranded oligonucleotides and the array-sorting signal receptor are complementary oligonucleotides. By attaching array-sorting signals to the terminus probes, the methods of the invention may be used in such way that the hybridization terminus probe to the adapter-modified restriction fragments takes place in solution rather than on a solid phase (e.g., an array). In those embodiments of the invention employing array-sorting signals on the terminus probes a sorting array, i.e., an array of array-sorting signal receptors, is employed to be used in conjunction with the array sorting signals. By attaching an array-sorting signal receptor at a specific location on an array, the presence of an oligonucleotide having the cognate array-sorting signal may be detected. In those embodiments of the invention in which terminus probes are marked with an array sorting signal, a detectable label, e.g., a fluorescent dye, may be joined to the terminus probe by means of a primer extension reaction employing detectably labeled nucleotides (e.g., fluorescent dye labeled 2'3' dideoxynucleotide triphosphates). The array sorting signals are preferably selected so as to minimize cross-hybridization between the different sorting signal and sorting signal receptors. In those embodiments of the invention employing oligonucleotides as sorting signals and sorting signal receptors, cross-hybridization may be avoided (or minimized) by selecting oligonucleotide sequences with minimal amounts of sequence homology between the different oligonucleotides.

Formation of Representative Restriction Fragments

Many different methods of producing representative restriction fragments may be used to practice the methods of the invention. These methods of producing representative restriction fragments may be used interchangeably with the different embodiments of the invention. In embodiments of the invention that include the step of amplifying adapter-modified representative restriction fragments, it is preferred that the method of generating representative restriction fragments be a method that generates representative restriction fragments that are substantially the same length. Methods for generating representative restriction fragments of substantially the same length may employ type IIs restriction endonucleases as described below in this section.

Methods of preparing representative restriction fragments include the technique of sequential restriction endonuclease digestion with two restriction endonuclease (having different recognition sites) as applied to immobilized DNA fragments. For the sake of convenience, this technique may be referred to as "sequential restriction digestion." Examples of sequential restriction digestion include the following method and variations thereof. cDNA is prepared from an RNA preparation of interest. The cDNA is immobilized on a solid phase. A large representative sample of the cDNA components of the cDNA preparation are immobilized at the same end of the cDNA molecule (typically the end of the cDNA corresponding to the mRNA polyA tail is immobilized). The immobilized cDNA is then digested with a first restriction endonuclease. The released, i.e., not bound, restriction fragments may then be washed away. Thus, the restriction endonuclease digestion process results in the production of an immobilized cDNA fragment having a terminus generated by a restriction endonuclease. A first adapter may optionally be ligated to the cDNA termini produced by the first restriction enzyme at this time. The immobilized cDNA is then digested with a second restriction enzyme having a different recognition site than the first restriction endonuclease. A second adapter is then ligated to the cDNA termini produced by the second restriction endonuclease. The released cDNA restriction fragments, each having termini produced by different restriction enzymes, are then collected and may subsequently be joined to adapters specific for each of the two termini. If an adapter had not been previously ligated to the termini produced by the first restriction endonuclease digestion, then first adapters are ligated to these termini. After the second adapter has been ligated, formation of adapter-modified representative restriction fragments has been completed.

The cDNA fragments may be immobilized to a solid phase at a predetermined end of the cDNA by a variety of methods, provided such methods do not substantially interfere with subsequent restriction endonuclease or ligation reactions. In a preferred embodiment of the invention, cDNA is synthesized using a biotinylated polyT primer to initiate first strand synthesis (priming from the RNA polyA tail). The biotinylated portion of the cDNA is then complexed with immobilized streptavidin or avidin. Of course, many specific binding pairs, e.g., antibody-hapten pairs, may be substituted for avidin-biotin to achieve the same immobilization effect. The solid support may be of any of a variety of forms such as beads, sheets, membranes, chips, fiber, and the like. Similarly, the solid support may be formed of any of a number of materials compatible with immobilization of nucleic acids, including, but not limited to, glass or polymers, e.g., polystyrene, polyacrylamide, polycarbonate, polyethylene, polypropylene, agarose, and the like.

Most restriction endonucleases are suitable for use in the restriction endonuclease digestion steps of the subject method. Restriction endonucleases are widely available commercially, and procedures for using them are well known to persons of ordinary skill in the art of molecular biology. Suitable restriction endonucleases may produce either blunt ends or overhanging ends.

Type IIs restriction endonucleases may also be used as a restriction endonuclease in sequential restriction endonuclease digestion. Type IIs restriction endonuclease have recognition sites that are different than the cleavage site. Because Type IIs restriction endonucleases are of particular interest because they may be used to produce small representative restriction fragments of a uniform size because the property of type IIs enzymes to cleave at a fixed distance from the recognition site, irrespective of the cleavage sequence. To use a type IIs restriction endonuclease for sequential restriction endonuclease digestion, a first adapter having Type IIs restriction endonuclease recognition site may be employed. For example, after digestion of immobilized cDNA fragments with a first restriction endonuclease, an adapter having a Type IIs restriction endonuclease recognition site is ligated to the immobilized restriction fragments, the Type IIs enzyme is then added, the dually digested restriction fragments are collected, and a second adapter is added (a polymerase catalyzed "filling-in" step may be used depending on the particular Type IIs enzyme employed).

In order to maximize the degree of representation of an mRNA population among the representative restriction fragments. The initial cDNA preparation obtained from the cells of interest may be split into two portions and digested with the first and second restriction endonucleases in both possible temporal orders, i.e., representative restriction fragments are formed employing both possible orientations. For example, a cDNA population could be split into two fractions and immobilized at the 5' end on separate sets of streptavidin derivatized magnetic beads (sets A and B). Set A is first digested with Hind III, washed, and then digested with EcoRI. Set B is first digested with EcoRI, washed, and then digested with Hind III. Thus, the representative fragments from set A contains fragments from RNA transcripts that have an EcoRI site closer to the 5' end than the Hind II site. Similarly, the representative fragments from set B contains fragments from RNA transcripts that have a Hind III site closer to the 5' end than the EcoRI site. Thus, by splitting the cDNA preparation into two portions and digesting with restriction enzymes in both temporal order, the degree of representation may be greatly increased. Subsequent analysis by the subject methods employing internal fragment probes and terminus probes may be performed separately on the dual preparations of representative restriction fragments.

Another method of deriving unique polynucleotide fragments from larger polynucleotides is described in Sherman in U.S. Pat. No. 5,712,126 (Weisman and Prashar), which is incorporated by reference herein. An example of the method of producing representative restriction fragments as described in U.S. Pat. No. 5,712,126, involves selectively amplifying the 3' portion of an mRNA by (a) priming first strand cDNA synthesis with a primer that hybridizes to a polyA tail and has a 5' non-hybridizing sequence region that can be used for priming amplification, (b) synthesizing the second strand, (c) cleaving the double-stranded cDNA with a restriction endonuclease, (d) ligating an adapter to the cleavage fragments, wherein the adapter consists of two partially hybridized nucleic acid strands, wherein portions of the two strands are non-complementary to each other and portions of the two strands are complementary to each other, (e) amplifying the ligated cleavage fragments using a first primer whose sequence comprises at least a portion of the 5' sequence of the oligonucleotide primer of step (a) and a second primer with a sequence that comprises at least a portion of the sequence of one strand of the adaptor in the non-complementary portion, thereby selectively amplifying a DNA fragment comprising sequence complementary to a 3' end of the mRNA.

Addition of Adapters

Adapters are joined to the termini of representative restriction fragments in most embodiments of the invention. The adapters may be joined to the termini in the same joining reaction or in two joining reactions (e.g., ligation) performed sequentially. Two adapters may be joined to a representative restriction, such that a single adapter is joined to each terminus. The two adapters are different from one another. However, the two adapters may be sufficiently similar to one another so as to permit annealing and amplification with a single primer oligonucleotide rather than a pair of two different primers. Methods for joining adapters to restriction fragments are well known to those of ordinary skill in the art. Guidance in using adapters can be found in, among other places, U.S. Pat. No. 5,693,245.

Nucleic Acid Amplification

Adapter-modified representative restriction fragments may be amplified by a variety of primer-dependent polynucleotide amplification techniques. A variety of primer-dependent polynucleotide amplification techniques may be used for amplification. Such techniques include strand displacement amplification, 3SR amplification, and the like. The polymerase chain reaction (PCR) is particularly preferred for amplifying the adapter-modified representative restriction fragments. The polymerase chain reaction is described in, among other places, Diffenbach and Dveksler, *PCR Primer* Cold Spring Harbor Press, Cold Spring Harbor, N.Y. (1995) and U.S. Pat. Nos. 4,683,202; 4,683,195; 4,800, 159; 4,965,188; and 5,333,675.

In embodiments of the invention employing polynucleotide amplification, the primers for use in the polynucleotide amplification primers are selected so a to work in conjunction with the adapters used in the given embodiment. One or more different primers may be used for a given adapter. The primers are selected so as to specifically anneal to portions of the adapters that have been joined to the representative restriction fragments.

Hybridization of Terminus Probes to Representative Restriction Fragments

A terminus probe of a known sequence may be hybridized to a representative restriction fragment (including adapter-modified representative restriction fragments and amplification products thereof) using conventional nucleotide acid hybridization techniques. Examples of nucleic acid hybridization techniques can be found, among other places in Sambrook et al., *Molecular Cloning* Cold Spring Harbor Press, Cold Spring Harbor, N.Y. (1989). Nucleic acid hybridization parameters, e.g., time, temperature, salt concentrations, etc., may be varied to optimize the desired result.

Arrays

Other embodiments of the invention include oligonucleotide arrays having a set of oligonucleotide features, wherein the oligonucleotides of each feature have a constant region and variable region. The variable region is joined directly to the constant region at the 3' end of the constant region. The set of oligonucleotide features on an array of the invention includes all possible variations (i.e., a complete set of variations) of the nucleotide sequence of the variable region. The constant region is functionally constant between the different features of the subject arrays. The term "functionally constant" as used herein refers the property of either (1) being identical, or (2) being identical with respect to the portion of the constant region that is designed to hybridize to a representative restriction fragment or an adapter-modified representative restriction fragment. In the second case, additional nucleotide may be present on the 5' end of the oligonucleotides that form a feature. Both the constant region and the variable may vary in length in accordance with the particular embodiment of the invention. The length of the variable region is preferably between 3 and 25 nucleotides in length, 3–12 being more preferred. In a most preferred embodiment of the invention, the variable region of the features is five bases in length. Because a complete set of features comprise all possible nucleotide base sequence variations of the variable region, the number of features that constitute a complete set will vary in accordance with the (the number of possible bases raised to the power of the length in a nucleotide). Thus, in embodiments of the invention employing a five base variable region, a set of array features comprises $4^5=1024$ features. The length of the constant region is sufficient to hybridize to the selected restriction endonuclease recognition site of representative restriction fragments and to either all or part of the strand of the adapter joined to the selected restriction endonuclease recognition site of the representative restriction fragments and to either all or part of the strand of the adapter joined to the selected restriction endonuclease recognition site of a representative restriction fragment. The nucleotide base sequence of the constant region may or may not be perfectly complementary to the relevant portion of the adapter modified representative restriction fragments. However, it is preferred to use hybridization conditions that require perfect complementarily. The constant regions are of sufficient length and of the proper nucleotide base composition to permit them to hybridize to a selected end of the adapter-modified representative restriction fragments. Upon hybridization with an adapter-modified representative restriction fragment, the double-stranded region formed between the adapter-modified representative restriction fragment and the constant region of the feature terminates at the nucleotide of restriction recognition site of the hybridized representative restriction fragment.

Kits

The invention also includes kits for performing one or more of the different methods for analyzing polynucleotide population described herein. Kits generally contain two or more reagents necessary to perform the subject methods. The reagents may be supplied in pre-measured amount for individual assays so as to increase reproducibility.

In one embodiment, the subject kits comprise adapters and primers for use with adapters to amplify adapter-modified restriction fragments. Kits may further comprise arrays of terminus probes for use in conjunction with the adapters. Other embodiments of the subject kits include arrays of terminus probes and sets of internal fragment probes for use in conjunction with the terminus probes of the array. Still other embodiments of the subject kits include kits that comprise (1) sorting-signal receptor arrays, and (2) terminus probes wherein the probes are appropriately marked with sorting signals for use in conjunction with the sorting signal receptor array. Probes of the subject kits may be marked with detectable signals suitable for use in the subject methods. The kits of the invention may also include one or more additional reagents required for various embodiments of the subject methods. Such additional reagents include, but are not limited to: restriction enzymes, DNA polymerases, buffers, nucleotides, and the like.

Incorporation By Reference

All publications, patent applications, and patents referenced in the specification are herein incorporated by reference to the same extent as if each individual publication or patent application was specifically and individually indicated to be incorporated by reference.

Equivalents

All publications, patent applications, and patents mentioned in this specification are indicative of the level of skill of those skilled in the art to which this invention pertains. Although only a few embodiments have been described in detail above, those having ordinary skill in the molecular biology art will clearly understand that many modifications are possible in the preferred embodiment without departing from the teachings thereof. All such modifications are intended to be encompassed within the following claims. The foregoing written specification is considered to be sufficient to enable skilled in the art to which this invention pertains to practice the invention. Indeed, various modifications of the above-described modes for carrying out the invention which are apparent to those skilled in the field of molecular biology or related fields are intended to be within the scope of the following claims

What is claimed is:

1. A method of analyzing a polynucleotide, said method comprising forming a restriction fragment from the polynucleotide, wherein the restriction fragment has a first and second terminus and at least one of the termini is generated by a restriction endonuclease, joining a first adapter to a terminus of the restriction fragment, whereby an adapter-modified restriction fragment is produced, and hybridizing a terminus probe to a single strand of the adapter-modified restriction fragment at a position including the terminus generated by the restriction endonuclease, wherein the terminus probe has a constant and a variable region.

2. The method according to claim 1, comprising, combining (i) the nucleotide sequence information from the terminus probe with (ii) the nucleotide sequence of the recognition site of the restriction endonuclease used to produce the terminus, so as to produce an identifier sequence.

3. The method according to claim 1 wherein the polynucleotide is a cDNA.

4. The method of claim 1, wherein the polynucleotide is derived from genomic. DNA.

5. The method of claim 3, wherein the restriction fragment is a representative restriction fragment.

6. The method of claim 1, wherein the identifier sequence comprises an SNP.

7. A method according to claim 1, wherein the terminus probe is a feature of an oligonucleotide array.

8. The method of claim 6, wherein the variable region of the terminus probes are 1 to 10 nucleotides in length.

9. The method of claim 1, said method further comprising the step of extending the terminus probe.

10. The method of claim 9, wherein the terminus probe is extended with a chain-terminating nucleotide.

11. The method of claim 10, wherein the chain-terminating nucleotide is fluorescently labeled.

12. The method of claim 10, said method comprising,
combining (i) the nucleotide sequence information from the terminus probe with, (ii) the nucleotide sequence of the recognition site of the restriction endonuclease used to produce the terminus, so as to produce an identifier sequence, and (iii) the base information from a chain terminating nucleotide incorporated in the chain extension reaction.

13. A method according to claim 1, wherein the terminus probe comprises an array sorting signal.

14. The method of claim 13, further comprising the step of extending the terminus probe with a chain-terminating nucleotide.

15. The method of claim 14, wherein the chain-terminating nucleotide is fluorescently labeled.

16. The method of claim 11 further comprising contacting the array-sorting signal with a sorting signal receptor array.

17. The method of claim 13, wherein the array sorting signal is a polynucleotide.

18. The method of claim 16, further comprising the step of extending the terminus probe with a chain-terminating nucleotide, wherein the extension takes place on a terminus probe that is bound to the sorting signal array.

19. The method of claim 13, said method comprising,
combining (i) the nucleotide sequence information from the terminus probe with, (ii) the nucleotide sequence of the recognition site of the restriction endonuclease used to produce the terminus, so as to produce an identifier sequence, and (iii) the base information from a chain terminating nucleotide incorporated in the chain extension reaction.

20. A method according to claim 5, wherein the representative restriction fragment is generated by a method comprising the steps,
immobilizing the polynucleotide on a solid support,
contacting the polynucleotide with a first restriction endonuclease, whereby an immobilized restriction fragment is produced, and
purifying the immobilized restriction fragment.

21. The method of claim 20, further comprising,
contacting the immobilized restriction fragment with a second restriction endonuclease, whereby the representative restriction fragment is produced, and purifying the representative restriction fragment.

22. The method according to claim 21, further comprising,
joining a linker to the terminus produced by the first restriction enzyme on the immobilized restriction fragment, whereby an adapter-modified immobilized restriction fragment was produced, and
contacting the adapter-modified immobilized restriction fragment with a second restriction endonuclease, whereby the representative restriction fragment is produced.

23. The method of claim 24, wherein the adapter comprises a type IIs restriction site and the second restriction endonuclease is a type IIs restriction endonuclease recognizes the type IIs restriction site in the adapter and cleaves within the immobilized restriction fragment.

24. The method of claim 1, said method further comprising,
joining a second adapter to the second terminus of the restriction fragment, amplifying the restriction fragment, wherein the amplification process uses a first amplification primer that anneals to the first adapter and a second amplification primer that anneals to the second adapter, wherein the amplification process takes place prior to the hybridization of the terminus probe.

25. The method of claim 24, wherein the at least one of the amplification primers is a selective primer.

26. The method of claim 25, wherein the first and second primers are selective primers.

27. The method of claim 1, wherein the polynucleotide for analysis is produced by amplifying a portion of a cDNA preparation or a portion of a genomic DNA preparation.

* * * * *